United States Patent [19]

Mende

[11] 4,145,411

[45] Mar. 20, 1979

[54] PRESSURIZED FOAMING SHAVING COMPOSITION

[75] Inventor: William C. Mende, Neshanic, N.J.

[73] Assignee: Colgate-Palmolive Company, New York, N.Y.

[21] Appl. No.: 660,295

[22] Filed: Feb. 23, 1976

Related U.S. Application Data

[63] Continuation of Ser. No. 503,237, Sep. 5, 1974, abandoned, which is a continuation of Ser. No. 305,865, Nov. 13, 1972, abandoned.

[51] Int. Cl.$^2$ .................. A61K 7/15; A61L 9/04
[52] U.S. Cl. .................. 424/45; 424/47; 424/73
[58] Field of Search .................. 424/45, 47, 73

[56] References Cited

U.S. PATENT DOCUMENTS

| | | | |
|---|---|---|---|
| 2,968,628 | 1/1961 | Reed | 252/305 |
| 3,240,396 | 3/1966 | Friedenberg | 252/DIG. 13 |
| 3,563,903 | 2/1971 | Schmadel et al. | 252/DIG. 13 |
| 3,574,118 | 4/1971 | Baker | 424/73 X |
| 3,705,855 | 12/1972 | Marschner | 424/73 UX |

OTHER PUBLICATIONS

Sagarin, Cosmetics Science and Technology, 1957, p. 405.

*Primary Examiner*—Dale R. Ore
*Attorney, Agent, or Firm*—Richard N. Miller; Murray M. Grill; Herbert S. Sylvester

[57] ABSTRACT

An improved pressurized foaming shaving composition in a valved container adapted to maintain the composition under pressure and to dispense it upon opening of the valve which comprises an aqueous medium, an anionic surface active agent such as soap, a foam stabilizer such as a $C_{12}$–$C_{18}$ fatty acid alkanolamide, a propellant and a mixture of 0.25–1% by weight of mineral oil, 0.005–0.025% by weight of lanolin and 0.001–0.006% of urea, said mixture being effective to provide a thicker, richer foam and to improve the feel of the shaved skin. Optionally, an additional foam stabilizer such as glycerol, propylene glycol or sorbitol is included in the composition.

1 Claim, No Drawings

PRESSURIZED FOAMING SHAVING COMPOSITION

This is a continuation, of application Ser. No. 503,237 filed Sept. 5, 1974 which is a continuation of application Ser. No. 305,865, filed Nov. 13, 1972, both now abandoned.

This invention relates to pressurized shaving compositions. More particularly, it is of such compositions and methods for their manufacture, wherein there is included a novel combination of substances which improve the quality of the shave, resulting in a moist, comfortable, easy shave which leaves the skin feeling smooth, soft and conditioned. The particular combination of substances when employed in the described proportions also surprisingly enhances the shaving foam making it thicker and richer.

The present invention of an improved shaving composition results in excellent shaves which are smooth, close, clean and comfortable and the shaved skin is left feeling soft and conditioned. Such results have been confirmed by in vivo tests against a previously acknowledged superior shaving cream.

In accordance with the present invention a pressurized foaming shaving composition in a valved container that is adapted to maintan the composition under pressure and dispense it when desired, upon opening of the valve thereof, comprises an organic liquefied gas propellant to pressurize the composition in the container and aid in discharging it therefrom, an aqueous medium, an anionic surface active foaming agent, a foam stabilizer and a mixture of mineral oil, lanolin, and urea in amounts such that the final shaving cream base contains about 0.25–1% of the mineral oil, about 0.005–0.025% of the lanolin, and about 0.001–0.006% of the urea. The invented compositions may be self-heating, if desired, but although such products soften hairs more quickly, they are not necessary for the attainment of the desired results of this invention.

The major constituent of the present shaving composition is an aqueous medium in which the other components are dissolved, emulsified or dispersed. It also often functions as a reaction medium and to some extent may participate in reactions, the principal of which is the neutralization of soap or other synthetic detergent acid(s). Minor proportions of solvents may be present in the medium, as may be dissolved salts usually in small or trace quantities, but it is preferred that the aqueous medium be water alone or essentially water. To avoid objectionable reactions during manufacture or storage and to maintain a desired whiteness or other color in the product, the presence of dissolved material such as inorganic salts will preferably be minimized. Thus, distilled or, preferably, deionized water will normally be used. The various solvents that may be present in the aqueous medium are usually limited to the extent of no more than 20% of the water content, preferably less than 10% and most preferably less than 5%, but usually no solvents will be present. Among acceptable solvents may be named the lower alcohols, such as those of 1 to 4 carbon atoms, preferably those of 2 to 3 carbon atoms, e.g., ethanol.

To produce the desired foam a surface active foaming agent will be employed. The preferred foaming materials will be anionic surface active compounds, such as the anionic detergents. Of these, the higher fatty acid soaps are preferable, especially those in which the soap-forming material is a mixture of an alkanolamine, such as triethanolamine, and alkali metals so that the soaps made are water soluble. At least a portion of the soap will advantageously be an alkanolamine soap. The water soluble soaps may be prepared by the saponification of fatty acids, natural oils and fats or mixtures thereof. The higher fatty acids are those of 12 to 18 carbon atoms. Preferably the higher fatty acid soaps will be mixed sodium, potassium and triethanolamine soaps of mixed stearic, palmitic and coconut oil fatty acids; in other words, the higher fatty acid soaps will be essentially saturated soaps.

In addition to the higher fatty acid soaps, other synthetic anionic organic detergents may be utilized. In some cases these will be employed in partial replacement of the soaps and in other, less preferred, instances may completely replace the soaps. The synthetic anionic detergents will usually include a higher aliphatic or alkyl moiety, preferably linear, and preferably terminally joined to the hydrophilic moiety which will most frequently be a sulfuric or sulfonic acid salt, with the saltforming ion being alkali metal, ammonium or di- or tri-lower alkanolamine wherein the lower alkanolamine is of 1 to 4 carbon atoms. Among the useful anionic detergents are the higher alkyl sulfates, higher alkyl sulfonates, higher alkyl benzene sulfonates, ethoxylated higher fatty alcohol sulfates, monoglyceride sulfates, higher fatty acid amides of amino-lower carboxylic acids, such as sodium lauroyl sarcoside, phosphates and phosphonates corresponding to the above mentioned sulfates and sulfonates, and sulfates and sulfonates of the wel-known nonionic surface active agents, such as those of polyoxyethylene glycols, of block copolymers of ethylene oxide and propylene oxide, chain terminated with propylene glycol and of polyethoxylated middle alkyl phenols. The above listing is only illustrative and additional listings of suitable synthetic anionic detergents and surface active agents which are useful in the present compositions may be found in the text *Detergent and Emulsifiers*, 1969, by McCutcheon and in *Surface Active Agents and Detergents*, Vol. II (1958), by Schwartz, Perry and Berch. Specific examples of useful anionic synthetic organic detergents or surface active agents for inclusion in this formula are: triethanolamine lauryl sulfate; linear dodecyl benzene sodium sulfonate; potassium coconut oil monoglyceride sulfate; ammonium paraffin sulfonate; and ammonium polyoxyethylene stearyl alcohol sulfate.

Accordingly, a foam stabilizer or mixture of such stabilizers is also advantageously employed. Such materials may include organic gums and colloids, serving as thickening agents to maintain the foam in the shape in which it was applied, but it will often be found preferable to utilize the lower alkanolamides of higher fatty acids for this purpose. The best of these is lauric-myristic diethanolamide wherein the fatty acid of the amide is a mixture of lauric and myristic acids, usually in a proportion of 1:3 to 3:1 and preferably about 1:1. Thus, such material is really a mixture of two different diethanolamides but is generally named for convenience as lauric-myristic diethanolamide or LMDEA. Other dialkanolamides of higher fatty acids are also acceptable foam stabilizers. These are diethanolamides of fatty acids of 12 to 18 carbon atoms, preferably of saturated fatty acids, and of mixtures thereof. Of such fatty acids, lauric, myristic, palmitic and stearic acids are most preferred. The lower alkanols may be of 1 to 4 carbon atoms, preferably of 1 to 3 carbon atoms and most preferably of 2 to 3 carbon atoms, e.g., ethanol and isopropanol. In addition to the dialkanolamides, corresponding monoethanolamides are also useful, to a lesser extent. In such compounds the higher fatty acid and lower alkanol moieties may be the same or mixed. Examples of such other foam stabilizers include coconut oil fatty acids monoethanolamide; hydrogenated tallow fatty acids diisopropanolamide; lauric di-n-propanolamide and stearic monoethanolamide. There may be mixed with such materials the known thickening agents such as the natural and synthetic organic gums, e.g., carageenan, gum tragacanth, alginates, gelatin, sodium carboxymethyl cellulose, polyvinyl alcohol and polyvinyl pyrrolidone. It has been found that in the present compositions additional foam stabilizing effects may be obtained by the inclusion of short chain diols and/or triols. Of these, the most useful are propylene glycol and glycerol, with the former being preferred. Sorbitol can also be present.

A propellant material is used to pressurize the container and to assist in discharging the foaming shaving composition. A wide variety of such propellants is known in the aerosol industry, including carbon dioxide, nitrogen, nitrous oxide, argon, air and other inorganic or inert gases, but to obtain the desired uniformly foaming compositions of the present invention. The lower hydrocarbon or lower halogenated hydrocarbon liquefied gas propellants, which are usually emulsified into the aqueous phase by means of the foaming agent, are those of 1 to 4 carbon atoms, preferably, with respect to the unhalogenated hydrocarbons, of 3 to 4 carbon atoms and, with respect to the halogenated hydrocarbon, of 1 to 3 carbon atoms. The hydrocarbons include n-butane, isobutane and propane and preferably are employed as a mixture of isobutane and propane, most preferably containing about 80 to 90 parts of isobutane and 10 to 20 parts of propane, with the preferable ratio being about 7:1. The halogenated hydrocarbons are preferably those in which the halogen is fluorine and/or chlorine. Most preferably, the halogenated propellants include fluorine in the molecule. Exemplary of such materials are monochlorotrifluoromethane, dichlorodifluoromethane, trichlorodifluoromethane, dichlorotetrafluoroethane, monochlorotetrafluoroethane, trichloromonofluoromethane, tetrachlorodifluoroethane and similar chlorofluoro-hydrocarbons having 1 to 3 carbon atoms per molecule. Of course, the halogenated hydrocarbons or the hydrocarbons are usually employed in mixtures and mixtures of halogenated and unhalogenated hydrocarbons may also be used. The mixing is normally done to regulate the pressure developed, solubilizing properties, corrosion prevention, emulsion formation, etc. The pressure developed by such a mixture will usually be 10 to 100 lbs./sq. in. and more commonly will be from 20 to 70 or 30 to 60 lbs./sq. in., most preferably about 50 lbs./sq. in. Pressures given are gauge pressures. Often, the propellant employed in mixture will include one having an equilibrium pressure at room temperature greater than 30 lbs./sq. in. and one having an equilibrium pressure at room temperature of less than 30 lbs./sq. in., with more of the latter being used, but other mixtures are also useful.

In addition to the constituents of the present compositions described above, various other materials are also advantageously added to give the product additional desired properties. For example, perfumes are usually employed and colorants may be desirable. Additional emollients, solvents, emulsifiers, suspending agents, buffers, conditioning agents, antioxidants, bactericides, proteins, etc., of known types, may be included in the composition for their particular effects. Normally, total contents of each of such adjuvants will be less than 10% of the product, preferably less than 5% thereof, and often there will be less than 1% of each present. It will generally be desirable to maintain the pH of the shaving cream in the range of 5 to 10.5, preferably from 7 to 10.5, and this may be done with the aid of buffering materials or control of acid and base contents.

The proportions of the various constituents in the preferred foaming shaving compositions to obtain superior results are from 70 to 90% of water, 5 to 15% of anionic surface active foaming agent, 0.5 to 3% of foam stabilizer, and 1 to 10% of propellant. Preferred ratios include from 75 to 85% of water, 7 to 13% of mixed higher fatty acid soaps, 0.7 to 1.5% of higher fatty acid dialkanolamides, and 2 to 7% of propellant mixture. In some compositions it may be desirable to have present 1 to 5% of an auxiliary foam stabilizer and emollient, such as propylene glycol, and a small amount such as 0.1 to 0.5% of another emollient, such as coconut oil. The normal percentage of perfume, which may be a mixture of essential oils, perfume aldehydes and ketones and suitable solvents and fixatives, will be from 0.1 to 3%. The proportion of high pressure propellant to low pressure propellant in the mixed propellant system will usually be less than one.

Surprisingly it has been found that when using the foam improvement system of the present invention, (i.e., the combination of mineral oil, lanolin, and urea) within the stated amounts, the foam is thicker than when using either less or more of this system. Thus, within the stated limits, the use of this system provides an improved, thicker, richer foam product while an excess of this system causes the formation of a thin, runny product.

The following example illustrates but does not limit the invention. Throughout the specification, unless otherwise indicated, temperatures are in ° C. and parts or percentages are by weight.

EXAMPLE I

A shave cream is formulated in accordance with the following specific amounts of the stated materials which are generally useful in accordance with the invention in the ranges set forth.

| INGREDIENTS | PREFERRED COMPOSITION | PREFERRED RANGE % |
|---|---|---|
| Water | 84.086 | 70-90 |
| Stearic Acid (Double Pressed) | 6.380 | 3-15 |
| Stearic Acid (Triple Pressed) | 0.440 | 3-15 |
| Triethanolamine | 0.128 | 0.05-3 |
| NaOH (38% solution) | 0.430 | QS |
| KOH (45.4% solution) | 2.300 | QS |
| Lauric Myrishe Diethanolomine | 0.890 | up to 4 |
| Propylene Glycol | 2.710 | up to 5 |
| White Mineral Oil Extra Light | 0.550 | 0.25-1 |
| Lanolin | 0.010 | 0.005-0.025 |
| Urea | 0.003 | 0.001-0.006 |
| Coconut Oil | 0.220 | up to 3 |
| Coconut oil Fatty Acid | 0.890 | up to 5 |
| Diammonium Phosphate | 0.020 | up to 1 |
| Oxyquinoline Sulfate | 0.001 | up to 1 |
| 1-Menthol | 0.022 | up to 1 |
| Methyl Parasept (Methyl-p-hydroxy-benzoate) | 0.018 | up to 1 |
| Propyl Parasept (Propyl-p-hydroxy-benzoate) | 0.002 | up to 1 |
| FD and C Red No. 3 (1% aqueous solution) | 0.150 | up to 2 |

| INGREDIENTS | PREFERRED COMPOSITION | PREFERRED RANGE % |
|---|---|---|
| Perfume | 0.750 | up to 3 |

The fatty acids react with the bases to form soaps.

To a valved aerosol container where are added 198.5 parts of the above composition and 5.7 parts of a mixture of 80 parts of isobutane and 20 parts of propane. The containers are shaken to aid in producing an emulsion. They are then packed and are ready for shipment and use.

Before use, the container is shaken slightly and the valve button is depressed, allowing dispensing of a desired amount of shaving foam, through the dispensing spout. Such foam when used, gives a superior, more moist and more comfortable and closer shave, and leaves the skin feeling smoother, softer, relaxed, and conditioned.

What is claimed is:

1. In a pressurized foaming shaving composition in a valved container which is adapted to maintain the composition under pressure and dispense it when desired upon opening the valve thereof, said composition consisting essentially of 1% to 10% by weight of a propellant to pressurize the composition in the container and aid in discharging it therefrom as a foam and a shave cream base consisting essentially of 70% to 90% by weight of an aqueous medium selected from the group consisting of water and water containing up to 20% by weight of an alcohol containing 2 to 3 carbon atoms and having dissolved, emulsified or dispersed therein 5% to 15% by weight of an anionic surface active foaming agent and, optionally, 0.5% to 3% by weight of a foam stabilizer selected from the group consisting of a fatty acid alkanolamide containing 12 to 18 carbon atoms in the fatty acid, organic gum, an organic colloid, propylene glycol, glycerol and sorbitol, the improvement wherein said shave cream base contains a mixture of about 0.25 to 1% mineral oil, about 0.005 to 0.025% of lanolin and about 0.001 to 0.006% of urea to thicken the foam of the composition dispensed from the container, the proportions of said mixture being based upon the shave cream base.

* * * * *